United States Patent [19]

Searle

[11] 4,380,400
[45] Apr. 19, 1983

[54] COMBUSTIBLE GAS ANALYZER

[75] Inventor: John L. Searle, Camden, N.J.

[73] Assignee: Honeywell Inc., Minneapolis, Minn.

[21] Appl. No.: 244,538

[22] Filed: Mar. 17, 1981

[51] Int. Cl.³ ............................................. G01N 25/22
[52] U.S. Cl. ....................................................... 374/37
[58] Field of Search ............... 73/190 CV; 422/51, 54, 422/98

[56] References Cited

U.S. PATENT DOCUMENTS

| | | |
|---|---|---|
| 3,001,550 | 9/1961 | Engel et al. |
| 3,013,790 | 12/1961 | Anderson et al. |
| 3,047,010 | 7/1962 | Rothfuss |
| 3,137,312 | 6/1964 | Hanes |
| 3,139,899 | 7/1964 | Schwerter |
| 3,393,562 | 7/1968 | Breedlove ............................ 73/190 |

FOREIGN PATENT DOCUMENTS 8151 2/1980 European Pat. Off. .............. 73/190

*Primary Examiner*—Herbert Goldstein
*Attorney, Agent, or Firm*—Lockwood D. Burton; Mitchell J. Halista

[57] ABSTRACT

A combustible gas analyzer for determining the calorific content of a combustible gas uses a constant flow rate air supply and a constant pressure combustible gas supply to provide oxygen and gas for combustion. The regulated air is supplied directly to be mixed with the combustible gas. On the other hand, the combustible gas is passed through a series connection of a pressure regulator and a variable orifice or valve before mixing with the air supply. A feedback pressure to control the pressure regulator for the gas is obtained from the output of the valve. The mixture of air and gas is burned in a combustion chamber, and a zirconium oxide detector is arranged to measure the oxygen content of the combustion products to enable a predetermined oxygen level to be reached, e.g., stoichiometric combustion. The valve is operated by a valve control apparatus responsive to the output of the detector to maintain the preset oxygen level. The position of the valve is monitored as a representation of the calorific content of the combustible gas.

6 Claims, 1 Drawing Figure

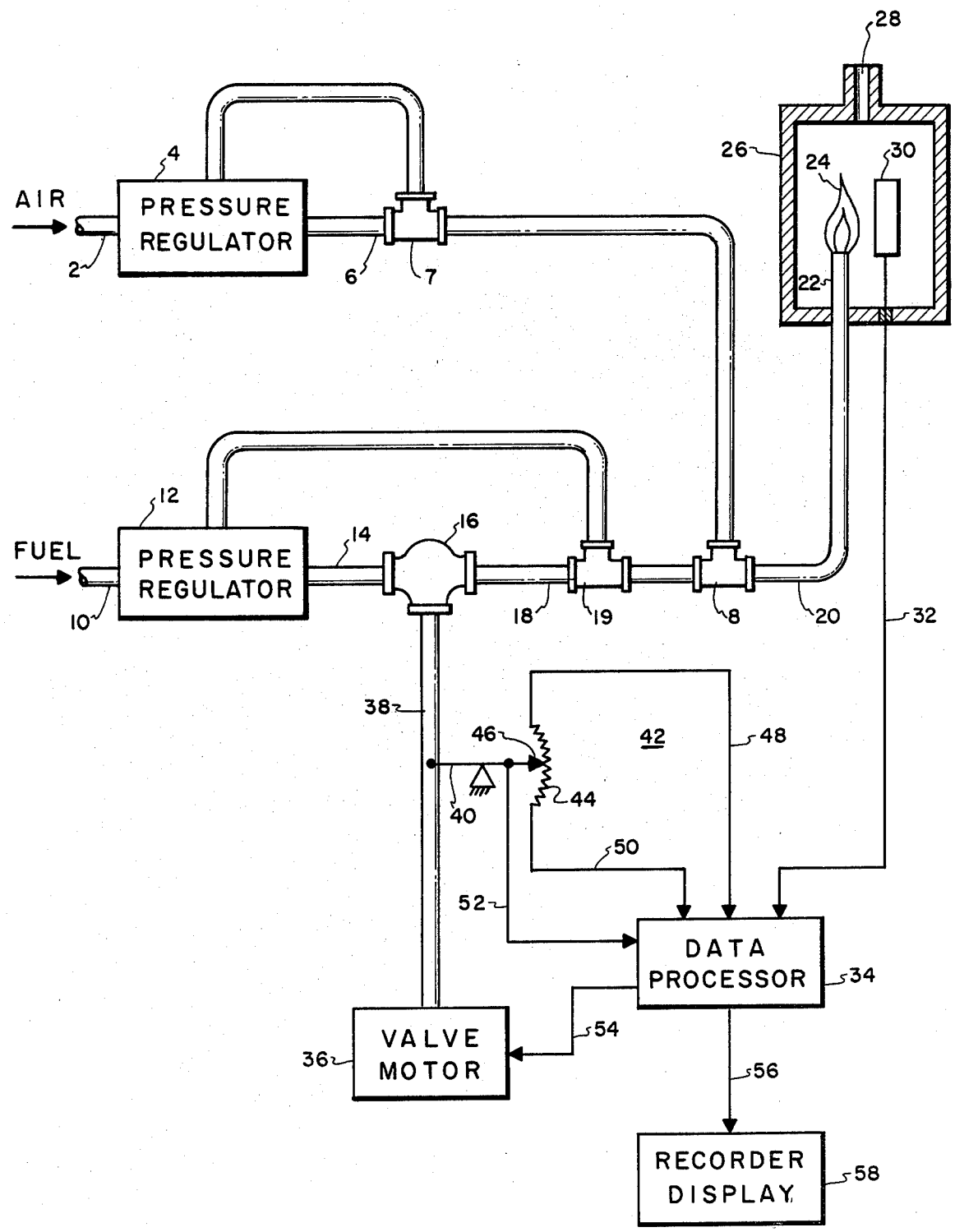

4,380,400

COMBUSTIBLE GAS ANALYZER

BACKGROUND OF THE INVENTION

1. Field of the Invention

The present invention is directed to combustible gas analysis apparatus. More specifically, the present invention is directed to a gas analysis apparatus for determining the calorific content of combustible gases.

2. Description of the Prior Art

The well-known Wobbe Index of a combustible gas is defined as the amount of heat released by a burner of constant orifice, McGraw-Hill Dictionary of Science, 1979 and stated mathematically by the following relationship:

$$W = H/\sqrt{SG}$$

where H is the caloric value of the gas per unit volume, e.g., $BTU/ft^3$, and SG is the specific gravity of the gas. The Wobbe Index is a quantity used in heating technology since different combinations of gases supplied to a gas heated apparatus under the same pressure provide equal heat production so that the apparatus need not be readjusted as long as the Wobbe indices are the same. If, for example, a mixture of gases from different sources is burned in an industrial operation, the gases must be mixed in such a proportion so that a gas is obtained having a constant Wobbe Index. One prior art method of determining the Wobbe Index of a combustion gas involves the combination of a calorimeter, a density meter and a computing circuit, e.g., a microprocessor. These parts while they may be combined into a single instrument produce an overall device which is very costly and exhibits sluggish operation whereby rapid changes in the gas mixture Wobbe Index are measured at a slow rate and the resulting correction, if necessary, is also applied at a correspondingly slow rate. It has been discovered that when gas mixtures having different compositions and different Wobbe Indices are burned with equal quantities of air, the oxygen content of the exhaust gas shows a direct correlation with the Wobbe Index. Accordingly, for purposes of measurement and control, it is not necessary to measure the Wobbe Index as such and it is sufficient to measure only the oxygen content in the exhaust gas. One prior art apparatus for producing this type of operation includes a sampling line containing a flow control nozzle for withdrawing a gas sample, a means for adjusting the gas sample so that the pressure difference through the control nozzle has an adjustable constant value, a means for feeding a constant volume of air as a source of combustion oxygen into the gas stream sample, a combustion chamber, a burner in the combustion chamber to completely burn the gas-air mixture, an outlet for the burned gas from the combustion chamber and an oxygen sensor in the combustion chamber to sense the oxygen quantity of the exhaust gas. This oxygen content is a quantity which is correlated to the Wobbe Index of the measured gas. However, by actually measuring or providing a quantity which represents the Wobbe Index the thermal delivery rate, i.e., BTU/minute, can be obtained to control the industrial heating operation. On the other hand, since the Wobbe Index is only related to the actual BTU content of the combustible gas, the actual measurement of the calorific, e.g., BTU, content of the combustible gas would provide a quantity which is even more directly applicable to the control of industrial heating operation. Such a measurement would provide a more efficient means of control to a furnace requiring a constant BTU per minute input without regard to changes in gas supply composition, density and BTU content of the combustible gas.

SUMMARY OF THE INVENTION

An object of the present invention is to provide an improved combustible gas analyzing apparatus for determining the calorific content of a combustible gas.

In accomplishing this and other objects, there has been provided, in accordance with the present invention, a combustible gas analyzing apparatus having a first flow rate control means supplying means air at a predetermined flow rate, a second pressure control means supplying a combustible gas to be analyzed at a controlled pressure, the second control means having an input, an output and a pressure feedback, a combustion chamber, gas mixing means for introducing into the combustion chamber a combustible gas and air mixture, a detector means for detecting the oxygen content of the combustion products from the combustion chamber, ratio control means connected to the output of the second pressure control means for controlling the ratio of combustible gas and air supplied to the mixing means in response to a signal from the detector means indicative of the oxygen content of the combustion products to produce a preselected oxygen content of the combustion products, feedback means connected between the ratio control means and the gas mixing means to produce a pressure feedback signal for application to the pressure feedback of the second pressure control means, the ratio control means including a valve connected between the output of the second pressure control means and the feedback means and having a valve stem and a valve stem drive means for producing a movement of the valve stem in response to the signal from the detector means and valve stem movement monitoring means for producing a signal representative of the position of the valve stem produced by the movement effected by the valve stem drive means as an indication of the calorific content of the combustible gas.

BRIEF DESCRIPTION OF THE DRAWING

A better understanding of the present invention may be had when the following detailed description is read in connection with the accompanying drawing, in which the single FIGURE is a pictorial illustration of a combustible gas analyzing apparatus embodying an example of the present invention for determining the calorific content of the combustible gas.

DESCRIPTION OF THE PREFERRED EMBODIMENT

Referring to the single FIGURE in more detail, there is shown a combustible gas analyzing apparatus embodying an example of the present invention for determining the caloric content, e.g., BTU, of a combustible gas. An air supply (not shown) is arranged to supply air as a source of combustion oxygen through input pipeline 2. The pipeline 2 is connected to the input of a first conventional pressure controller or regulator 4 while the output of the pressure regulator 4 is connected to an output pipeline 6. The pressure controllers used herein have an input, an output and a feedback to which is applied a pressure feedback for controlling the pressure output of the controller. The output pipeline 6 is connected to a T-connector 7 for supplying a feedback pressure signal to the first pressure regulator 4 feedback input for controlling the output pressure from the pressure regulator 4 in the output pipeline 6. The output of the T-connector 7 is connected to one input of a mixing connector 8 through an output pipeline 9. In a conventional fashion, the pipeline 9 is arranged to contain a fixed orifice (not shown) which is the dominating downstream restriction in the flow line supplied by the output of the pressure regulator 4. Such a fixed orifice provides a means for achieving a constant flow rate of the air from the pressure regulator 4 to form therewith a constant flow rate air supply.

Concurrently, a supply of the combustible gas (not shown) is arranged to supply a fuel or combustible gas through a second input pipeline 10 which is connected to the input of a second pressure regulator 12. The output of the second pressure regulator 12 is applied through an output pipeline 14 to the input of a control valve 16. As in the case of the previously mentioned orifice in the pipeline 9, the valve 16 is arranged to provide an orifice which, while variable, is the dominating downstream restriction in the flowline supplied by the output of the second pressure regulator 12. Since a variation flow of the fuel gas is desired, a constant flow rate is not needed in contrast to the air flow rate provided by the orifice in the pipeline 9. The output of the control valve 16 is supplied through an output pipeline 18 to a T-connector 19 used to supply a feedback pressure signal to the feedback input of the second pressure regulator 12. The output of the T-connector 19 is connected to a second input of the mixing connector 8. An output of the mixing connector 8 is connected through a pipeline 20 to a burner jet 22 for producing a combustion flame 24.

The burner jet 22 and the combustion flame 24 are located within a combustion chamber or housing 26. Also located within the housing 26 would be a means for initiating the burning of the combustible gas by means of a spark or other device and a means for detecting the presence of the flame 24 to provide a control for the flame initiating device. Such devices are well-known in the art, and accordingly, have not been shown in the illustration of the single FIGURE drawing. The exhaust gases from the combustion chamber 26 are allowed to escape through a restricted exhaust port 28 in the wall of the combustion chamber 26. The aforesaid restrictions provided by the fixed restriction in the pipeline 9 and by the variable restriction of the valve 16 are each effective to provide a greater restrictive effect than that imposed by the other flowline elements, as previously mentioned, including the flow impediments imposed by the mixing connector 8, the burner 22 and the exhaust port 28. A conventional zirconium oxide detector 30 is located adjacent to the flame 24 to effect a detection of the oxygen content of the end products of the combustion process to determine a preselected combustion state, e.g., stoichiometric combustion. The output of the zirconium oxide detector 30 is applied over an output line 32 to an input of a data processing system 34 which may incorporate a suitable microprocessor.

The valve 16 is driven by a valve motor 36 connected thereto by a valve stem 38. The valve stem 38 is connected to an apparatus arranged to provide an indication of the position of the valve stem. An example of an apparatus providing such an indication includes a lever arm 40 attached to the valve stem 38 and arranged to drive a slider 46 of a potentiometer 42 across the resistance element 44 of the potentiometer 42. The resistance element 44 of the potentiometer is connected by electrical lines 48 and 52 to the data processor 34 while the slider 46 is connected by an electrical line 52 to the data processor 34. The data processor 34 is also arranged to use the input signal from the zirconium oxide detector 30 to produce a control signal on output line 54 for controlling the operation of the valve motor 36. Concurrently, the data processor 34 may be used to produce an output signal in response to a signal from the potentiometer 42 on a data output line 56 which is connected to a recorder display 58 for displaying the position of the valve stem 38 as an indication of the calorific content of the fuel gas being supplied through the fuel inlet line 10.

In operation, the air supply controlled through the first pressure regulator 4 is supplied to the mixing valve 8 in combination with the fuel gas supplied through the second pressure regulator 12 and the control valve 16. The combustion of the fuel gas in the presence of the air is effected by the flame 24 in the combustion chamber 26. The oxygen content of the combustion gases is detected by the zirconium oxide detector 30. Since the control valve 16 functions as a variable orifice, the feedback pressure from the T-connector 19 to the pressure regulator 12 provides a variable flow apparatus. Consequently, the output signal supplied to the recorder display on output line 56 is representative of the valve motor 36 and is a direct indication of the caloric content of the combustion or fuel gas. This is the result of having a short orifice, i.e., an orifice having a flow length which is less than the orifice diameter, e.g., a hole in a plate, which produces an effect dependent on the specific gravity of the fluid flowing therethrough as contrasted with a long orifice having an orifice length greater than the orifice diameter, e.g., a capillary, which produces an effect dependent on the viscosity of the fluid flowing therethrough.

In the combustible gas measuring arrangement of the present invention, the variable orifice produced by the valve 16 is the only significant restriction prior to the burner 22. In such an arrangement, the calorific, e.g., BTU, value of the gas being burned at the burner 22 will be altered if fuels of different specific gravity are introduced from the fuel line 10. In other words since:

$$H = W/\sqrt{SG}$$

then:

$$W = \frac{H}{\sqrt{SG}}$$

Accordingly, the measurement of the movement of the valve stem 38 is dependent on the specific gravity of the fuel and is, therefore, a direct indication of the Wobbe Index. However, by providing feedback pressure from the output of the valve 16, the system operation is made independent of specific gravity. Thus, any change in specific gravity would readjust the pressure equilibrium of the regulator 12 to compensate for a specific gravity whereby the valve stem position is a measure of calorific content. The valve 16 is operated by the data processor 34 by means of the valve motor 36 and the valve stem 38 to produce desired combustion state, e.g., stoichiometric combustion at the flame 24.

It should be noted that stoichiometric combustion is only one point on the combustion curve which may be used and only a repeatability is necessary by returning to the same point for each measurement. The combustion condition is detected by the sensor 30 as a result of the minimal amount of oxygen remaining in the combustion products from the flame 24. The calorific content of the fuel gas may be displayed on a suitable display or recorded as a record since the recorded display 58 may include a hard copy recorder as well as a display apparatus, e.g., cathode ray tube (CRT). It should be noted that, since the accuracy of the calorific content measurement is dependent on specific gravity of the fuel gas, the proportion of non-combustible gases therein, e.g., helium, will affect the accuracy of the measurement. Specifically, the relationship is an inversely proportional one, i.e., the greater the quantity of non-combustible elements, the lower will be the measurement accuracy. However, in a real life application of the present invention, e.g., gas user measurements, the non-combustible content is very small which provide a high measurement accuracy of the calorific content, e.g., 1%.

Accordingly, it may be seen that there has been provided, in accordance with the present invention, an improved gas analyzing apparatus for determining the calorific content of a combustible gas.

The embodiments of the invention in which an exclusive property or privilege is claimed are defined as follows:

1. A combustible gas analyzer comprising
   first pressure control means for supplying combustion air at a predetermined flow rate,
   second pressure control means for supplying a combustible gas to be analyzed at a controlled flow rate, said second control means having an input, an output and a pressure feedback,
   gas mixing means for mixing air from said first pressure control means and a combustible gas to be analyzed,
   valve means located at said output of said second control means for performing a valving operation on a flow of a combustible gas to be analyzed from said second control means, said valve means including a valve stem and a valve stem drive motor,
   feedback pressure means connected between an output of said valve means and said feedback of said second control means for providing a feedback pressure signal to said second control means to control the pressure of said combustible gas at said output of said second control means,
   combustion means connected to an output of said mixing means for producing a combustion of a mixture of said air and said combustible gas from said mixing means,
   detector means for detecting the oxygen content of combustion products from the combustion of said air and said combustible gas by said combustion means,
   control means responsive to said detector means for producing a control signal for controlling said valving operation of said valve means to achieve a preselected oxygen content of said combustion products,
   circuit means for applying said control signal to said valve motor to effect a corresponding motion of said valve stem,
   valve stem movement monitoring means connected to said valve stem for producing a signal representative of the position of said valve stem and
   display means for displaying said signal from said monitoring means as an indication of the calorific content of said combustible gas.

2. A combustible gas analyzer as set forth in claim 1 wherein said preselected oxygen content of said combustion products is representative of substantially stoichiometric combustion.

3. A method for analyzing a combustible gas to determine the calorific content of the gas including the steps of supplying air as a source of combustion oxygen at a constant flow rate, supplying a combustible gas, regulating the flow rate of the combustible gas in accordance with a pressure feedback signal, passing the regulated gas through a valve arranged to provide a variable restriction to the flow of the gas, deriving the feedback signal from the output of the valve, mixing the air and the output of the valve, burning the gas and air, detecting the oxygen content of the combustible products resulting from the burning of the gas and air, controlling the valve to affect the variable restriction in response to the detection of the oxygen content of the combustion products and monitoring the size of the valve restriction as an indication of the calorific content of the gas to be analyzed.

4. A method as set forth in claim 3 wherein the preselected oxygen content of the combustion products is effective to produce a substantially stoichiometric combustion of the combustible gas.

5. A method as set forth in claim 3 wherein the valve includes a valve stem and a valve stem drive means for varying the size of the variable restriction by a movement of the valve stem and the controlling of the valve includes the step of energizing the valve stem drive means to vary the size of the variable restriction while the step of monitoring the size of the valve restriction includes the step of monitoring the position of the valve stem.

6. A combustible gas analyzer comprising
   first pressure control means arranged to be connected to a source of air for supplying air as a source of combustion oxygen at a predetermined flow rate,
   second pressure control means for supplying a combustible gas to be analyzed at a controlled flow rate, said second control means having an input, an output and a pressure feedback,
   gas mixing means for mixing air from said first pressure control means and a combustible gas to be analyzed,
   valve means located at said output of said second control means for performing a valving operation on a flow of a combustible gas to be analyzed from said second control means, said valve means including a variable restriction and drive means for varying said restriction,
   feedback pressure means connected between an output of said valve means and said feedback of said second control means for providing a feedback pressure signal to said second control means to control the pressure of said combustible gas at said output of said second control means,
   combustion means connected to an output of said mixing for producing a combustion of a mixture of said air and said combustible gas from said mixing means, detector means for detecting the oxygen content of combustion products from the combustion of said air and said combustible gas by said combustion means, control means responsive to said detector means for producing a control signal for controlling said valving operation of said valve means to achieve a preselected oxygen content of said combustion products, circuit means for applying said control signal to said drive means to effect a corresponding variation of said variable restriction, monitoring means for monitoring the size of said restriction to produce a signal representative of the size of said restriction and display means for displaying said signal from said monitoring means as an indication of the calorific content of said combustible gas.

* * * * *